United States Patent [19]
Gefter et al.

[11] Patent Number: 5,169,939
[45] Date of Patent: Dec. 8, 1992

[54] CHIMERIC ANTIBODIES

[75] Inventors: Malcolm L. Gefter, Weston; Mark Ptashne; Jacqueline Sharon, both of Cambridge, all of Mass.

[73] Assignee: Massachusetts Institute of Technology & Pres. & Fellows of Harvard College, Cambridge, Mass.

[21] Appl. No.: 296,375

[22] Filed: Apr. 9, 1989

Related U.S. Application Data

[63] Continuation of Ser. No. 736,477, May 21, 1985, abandoned.

[51] Int. Cl.$^5$ .................. C07K 15/28; C07K 17/06
[52] U.S. Cl. ..................... 530/387.3; 530/387.7; 530/391.5; 530/391.9; 435/174; 435/188; 435/69.7; 435/194; 435/320.1
[58] Field of Search ............... 530/387, 388, 389, 390, 530/391, 387.3, 387.7, 391.5, 391.9; 435/188, 320.1, 174, 194, 69.7

[56] References Cited

U.S. PATENT DOCUMENTS

| | | | |
|---|---|---|---|
| 4,545,985 | 10/1985 | Pastan et al. | 424/85.91 |
| 4,642,334 | 2/1987 | Moore et al. | 424/85 |
| 4,675,382 | 6/1987 | Murphy | 530/350 |
| 4,816,397 | 3/1989 | Boss et al. | 435/68 |
| 4,816,567 | 3/1989 | Cabilly et al. | 530/387 |
| 4,892,827 | 1/1990 | Pastan et al. | 435/193 |
| 4,894,443 | 1/1990 | Greenfield et al. | 530/388 |
| 4,946,778 | 8/1990 | Ladner et al. | 435/69.6 |

FOREIGN PATENT DOCUMENTS

| | | |
|---|---|---|
| 0120694 | 3/1984 | European Pat. Off. |
| 0125023 | 11/1984 | European Pat. Off. |
| 0173494 | 3/1985 | European Pat. Off. |
| 8403103 | 8/1984 | PCT Int'l Appl. |
| 8403712 | 9/1984 | PCT Int'l Appl. |
| 8601533 | 3/1986 | PCT Int'l Appl. |
| 8303971 | 11/1983 | World Int. Prop. O. |
| 8400382 | 2/1984 | World Int. Prop. O. |

OTHER PUBLICATIONS

Cabilly et al., PNAS 81, 1984, pp. 3273-3277.
Nature 312, 1984, pp. 643-646, Boulianne et al.
Or et al., Biotechnology Newswatch, McGraw Hill, pp. 2-3 Mar. 1985.
Morrison, Science 229, 1985 pp. 1202-1207.
Raso et al., (1982) Cancer Research 42:457-64.
Kirwana et al. (1987) Biochem. Biophys. Res. Chammun. 1219(3):960-968.
Gascoigne et al., (1987) PNAS 84:2936-2940.
Becker et al. (1989) Cell 58:911-921.
*Immunology*, 2nd ed. L. E. Hood et al. The Benjamin/Cummings Publishing Company, Inc. Menlo Park, CA 1984, pp. 88-92.
Chisholm, *High Technology* 1983, pp. 57-63.
Sun et al., *Hybridoma* 5(1) 1986, pp. 517-520.
Gough, *TIBS* 6(8) 1981, pp.203-205.
Kameyama, Salbo Kogaku 4(12) 1985, pp. 1025-1035.
Sharon, J., M. L. Gefter, T. Mauser, S. L. Morrison, V. T. Oi, and M. Patshne: Expression of a $V_HC_K$ chimaeric protein in mouse myeloma cells. *Nature*, 309: 364-367 (1984).

(List continued on next page.)

*Primary Examiner*—Christine M. Nucker
*Assistant Examiner*—Kay Kim
*Attorney, Agent, or Firm*—Hamilton, Brooks, Smith & Reynolds

[57] ABSTRACT

Chimeric antibodies comprised of the variable region of an antibody chain contiguous with a polypeptide other than the constant region of that antibody chain are disclosed. Such chimeric antibodies can be comprised of the variable region of a chain of an immunoglobulin of selected specificity and an extrinsic polypeptide. In addition to the variable region of a chain of an immunoglobulin of selected specifity and an extrinsic polypeptide, the chimeric antibodies can include at least a portion of the constant region of an immunoglobulin chain.

42 Claims, 6 Drawing Sheets

OTHER PUBLICATIONS

Morrison, S. L., M. J. Johnson, L. A. Herzenberg and V. T. Oi: Chimeric human antibody molecules: Mouse antigen-binding domains with human constant region domains. *Proceedings of the National Academy of Sciences, USA*, 81: 6851-6855 (1984).

Boulianne, G. L., H. Hozumi and M. J. Shulman: Production of functional chimaeric mouse/human antibody: *Nature*, 312: 643-646 (1984).

Boulianne, G. L., N. Hozumi, C. Heusser and M. J. Shulman: The Production of Chimeric Mouse/Human Antibodies, Post #25, Int'l Symposium on Cellular and Molecular Biology of Neoplasia, Honey Harbor, Canada, presented Oct. 4, 1983.

Oi, V. T., S. L. Morrison, L. A. Herzenberg and P. Berg: Immunoglobulin gene expression in transformed lymphoid cells, *Proceedings of the National Academy of Sciences, USA*, 80: 825-829 (1983).

Munro, A.: Uses of chimaeric antibodies, *Nature*, 312: 597 (1984).

Ochi, A., et al.: Functional immunoglobulin M production after transfection of cloned immunoglobulin heavy and light chain genes into lymphoid cells, *Proceedings of the National Academy of Sciences, USA*, 80: 6351-6255 (183).

Neuberger, M. S. et al., *Nature, 312:604-608 (1984)*.

Neuberg, M. S. et al., *Nature*, 314:268-270 (1985).

Takeda, S. et al., *Nature*, 314:452-454 (1985).

Siekevitz et al., *Eur. J. Immunol.*, 12: 1023-1032 (1982).

CHIMERIC ANTIBODIES

FUNDING SOURCES

The work described herein was supported by grants from the National Institutes of Health, the American Cancer Society and the Damon Runyon—Walter Winchell Cancer Fund.

This is a continuation of co-pending application Ser. No. 06/736,477 filed on May 21, 1985, now abandoned.

FIELD OF THE INVENTION

This invention is in the field of molecular immunology.

BACKGROUND OF THE INVENTION

Antibody Structure

Antibodies exist in millions of different forms, each of which has a unique binding site for an antigen. The simplest antibodies are described as Y-shaped molecules with two identical antigen-binding sites, one located at the tip of each of the two arms of the Y (FIG. 1). Thus, antibodies are bivalent ligands capable of crosslinking function.

An antibody molecule is an assembly of four polypeptide chains: two identical light chains and two identical heavy chains, which are held together by disulfide bonds. There are five classes of antibodies, collectively referred to as immunoglobulins (Igs): IgA, IgD, IgE, IgG and IgM. Each class has a distinctive heavy chain which is responsible for the distinctive properties of the class. The heavy chains for the immunoglobulins in these five classes are, respectively, alpha, delta, epsilon, gamma and mu.

In addition to the five classes of heavy chains, there are two types of light chains: kappa and lambda. Either of these two types of light chains can be associated with any type of heavy chain. However, individual antibody molecules always have two identical light chains and two identical heavy chains. As a result, their antigen-binding sites are also identical.

Both the light and the heavy chains have distinct constant and variable regions. That is, they have distinct regions in which the amino acid sequences are the same or differ only slightly (the constant regions) and distinct regions in which the sequences are extremely variable (the variable regions). The variable region is located at the amino terminal portion of both the light and the heavy chains; the constant region is located at the carboxyl terminal portion of both types of chains. The variable region of the heavy chain ($V_H$) and the variable region of the light chain ($V_L$) associate to form the antigen-binding complexes.

The diversity of antigen binding sites is based on the variability of the amino acid sequences in those regions. However, it does not appear that the entire $V_L$ and $V_H$ regions contribute to the specificity of the antigen-binding site. Rather, each chain has three relatively small hypervariable regions, to which most of the variability in the variable regions is actually restricted. These three hypervariable regions define or form the binding site of antibodies and may consist of only 20 to 30 amino acids in the variable regions of each chain. The amino acid sequences of the rest of the variable region are relatively constant and form what is known as framework regions.

As indicated, both the light and the heavy chains have constant regions. However, the amino acid sequence in the constant region of heavy chains is approximately three times as long as the constant region sequence in light chains. It appears that a light chain has a single constant domain ($C_L$) and most heavy chains have three separate constant domains ($C_{H1}$, $C_{H2}$, $C_{H3}$). The epsilon and the mu chains apparently have four constant domains. The three (or four) constant domains of the heavy chain show considerable homology to each other and also to the light chain constant regions. The heavy chain constant domains (except $C_{H1}$) make up the $F_C$ region, which determines the antibody's other biological characteristics.

Genetic Determination of Antibody Structure

For each type of immunoglobulin chain (the kappa and lambda light chains and the heavy chains), there is a pool of genes. Each gene pool contains different variable (V) genes located upstream from one or more constant (C) genes. During B-cell development, one of the numerous V genes is translocated to a position close to a specific C gene. This must occur before immunoglobulin chain synthesis can be carried out. A single polypeptide chain is ultimately synthesized from the gene pool.

Two adjacent gene segments are known to encode the V region of light chains: the V-lambda gene segment, which encodes the amino terminal 97 amino acids, and the J-lambda gene segment, which encodes the remaining 13 amino acids of the V lambda region. The two are separated by an intervening DNA sequence or intron. The result is a V-lambda-J-lambda-intron-C-lambda sequence, which is transcribed into primary RNA. The introns are subsequently removed by RNA splicing and mRNA having contiguous V, J and C segments is produced. This mRNA is translated into light chain polypeptides.

Three gene segments code the V region of heavy chains. As is the case for the V region of light chains, a J gene segment ($J_H$) is involved. In addition, a segment (diversity or D) encoding amino acids in a hypervariable region of the V region is required. Recombination occurs to join a gene segment, a variable gene and a $J_H$ gene segment to produce a functional $V_H$ gene.

Coupling Antibodies to Proteins

Methods presently available for linking antibodies with proteins which act as drugs, toxins or other agents generally involve chemical coupling of the two components. These methods, however, cannot be effectively controlled and result in production of a variety of molecules because of the rand-om nature of the process. For example, mixing and polymerization of the antibody molecules occurs. For pharmacological purposes, it is highly desirable to produce definable molecules; presently available methods do not provide a reliable way of doing so. A method of coupling antibodies with proteins which avoids these drawbacks would not only provide a simpler means of joining them, but also result in definable (specific) antibody-protein combinations.

Disclosure of the Invention

This invention constitutes chimeric antibodies having at least one chimeric (recombinant) polypeptide chain. In general, the chimeric chain is comprised of the variable region of a chain of an immunoglobulin of selected specificity and an extrinsic polypeptide (e.g., one other than that comprising the constant region of the immunoglobulin). It is also possible for the chimeric antibody to be comprised of the variable region of a chain of an immunoglobulin of selected specificity; at least a portion of the constant region of an immunoglobulin chain; and an extrinsic polypeptide. In association with a counterpart light or heavy chain and its variable region, the chimeric chain provides a monovalent chimeric immunoglobulin molecule having the functional antigen-binding site. The variable region of each chain is derived from the same immunoglobulin to provide selected specificity. Divalent chimeric antibodies can be constructed by employing heavy chains which contain the appropriate portion of the constant region for disulfide bridging between chains to achieve divalency.

The chimeric antibodies of this invention are recombinant molecules in which the antigen binding site of an antibody is combined with extrinsic polypeptide, i.e., a polypeptide other than those from which the immunoglobulin binding site is derived. The joining of the antibody binding site to the foreign protein is accomplished by recombinant DNA techniques. Protein molecules which have binding, enzymatic, toxic or other properties useful for diagnostic or therapeutic purposes can be fitted with a specific antigen binding site of an antibody. This results in a so-called "smart" drug. The antibody binding site directs the drug to tissue sites which exhibit the cognate antigenic determinant of the binding site.

The chimeric antibodies are formed of chimeric or recombinant immunoglobulin chains. Variable regions of immunoglobulin chains retain their binding capability and specificity when joined, as part of a single polypeptide, to polypeptides other than their own constant region. Thus, the constant region of an immunoglobulin chain can be replaced or altered without affecting function dependent upon the variable region. The variable region can be linked to an extrinsic protein, either directly or through a peptide linker molecule or it can be linked to recombinant "constant" regions which constitute, at least in part, extrinsic protein. Such recombinant chains can be designed so that they retain the ability to associate with a corresponding light or heavy chain and form a complete antigen binding site.

Chimeric antibodies can be constructed in several different forms. The chimeric molecules can be monovalent (single binding site) or divalent (two binding sites) depending upon the design of the hybrid chains. A monovalent chimeric immunoglobulin, for example, can include a heavy chain comprising: 1) the variable region ($V_H$) of a heavy chain of an immunoglobulin of selected specificity; 2) the constant region ($C_L$) of a light chain of an immunoglobulin; and 3) an extrinsic polypeptide (X). This chain, associated with a light chain having a variable region of the same immunoglobulin, provides a monovalent chimeric antibody which can be represented by the formula: $V_H C_L X — V_L C_L$. The binding site specificity is conferred by the $V_H$ and $V_L$ regions which can be derived from the same immunoglobulin molecule. Because the variable regions of the heavy and the light chains are all that is necessary to form a functional antibody binding site, it is also possible for chimeric antibodies to include the variable region ($V_H$) of a heavy chain and no constant region ($C_L$) of a light chain. The monovalent chimeric antibody in this case can be represented by the formula: $V_H X — V_L$. The extrinsic polypeptide X may be linked to $V_H C_L$ or to $V_H$ by a peptide linker (e.g., one or more amino acid residues).

A divalent chimeric immunoglobulin can be comprised of a contiguous, hybrid heavy chain containing: 1) the variable region ($V_H$) of a heavy chain of an immunoglobulin of selected specificity; 2) a portion ($C_{H1}C_{H2}$) of the constant region of a heavy chain which includes the $C_{H1}$ constant domain and at least a portion of the $C_{H2}$ constant domain; and 3) at least the active portion of an extrinsic polypeptide (X). The $C_{H1}$ and $C_{H2}$ domains are necessary to provide the sulfide bridge which joins two heavy chains to form a divalent molecule. In these divalent molecules, each heavy chain is associated with a corresponding light chain to provide complete binding sites. The divalent chimeric immunoglobulin can be represented by the formula: $(V_H C_{H1} C_{H2} X — V_L C_L)_2$. Again, the extrinsic polypeptide may be linked to $V_H C_{H1} C_{H2}$ by a peptide linker.

The chimeric antibodies are formed by constructing, in an expression vector, the fused gene which codes for the hybrid chain of antibody. First, antibody genes are cloned. Antibody genes can be obtained from hybridoma cell lines which produce antibody of desired specificity. The cloned antibody gene for a selected chain is recombined to produce the desired chimeric chain. For example, to construct a chimeric antibody of the formula $V_H C_L X — V_L C_L$, the gene encoding the heavy chain of an antibody can be inserted into a cloning and expression vector. A DNA sequence encoding a light chain constant region can then be inserted 3' to the variable region of the heavy chain. The gene encoding the foreign polypeptide is inserted 3' to the constant region sequence, the translation termination sequence having been engineered out. This provides a fused gene encoding the hybrid chain $V_H C_L X$.

This fused gene construct can then be used to transform a recipient cell. Recipient cells can be either mammalian cells capable of antibody production (e.g., B lymphocytes, myeloma cells, hybridoma cells) or yeast or bacterial cells which are transformed with a vector having the constructed genes encoding the chimeric antibody and are capable of expressing them. The recipient cell can be one which expresses the counterpart chain for the hybrid ($V_L C_L$) either naturally or because it has been transformed to express the chain. Alternatively, the counterpart chain can be provided by a different cell and the two cells fuse to permit in vivo association in the two chains can be associated in vitro under appropriate conditions. Alternatively, gene sequences for both chains can be engineered into the same vector, which can be transformed into the above-mentioned cells.

BEST MODE OF CARRYING OUT THE INVENTION

Figure 1:
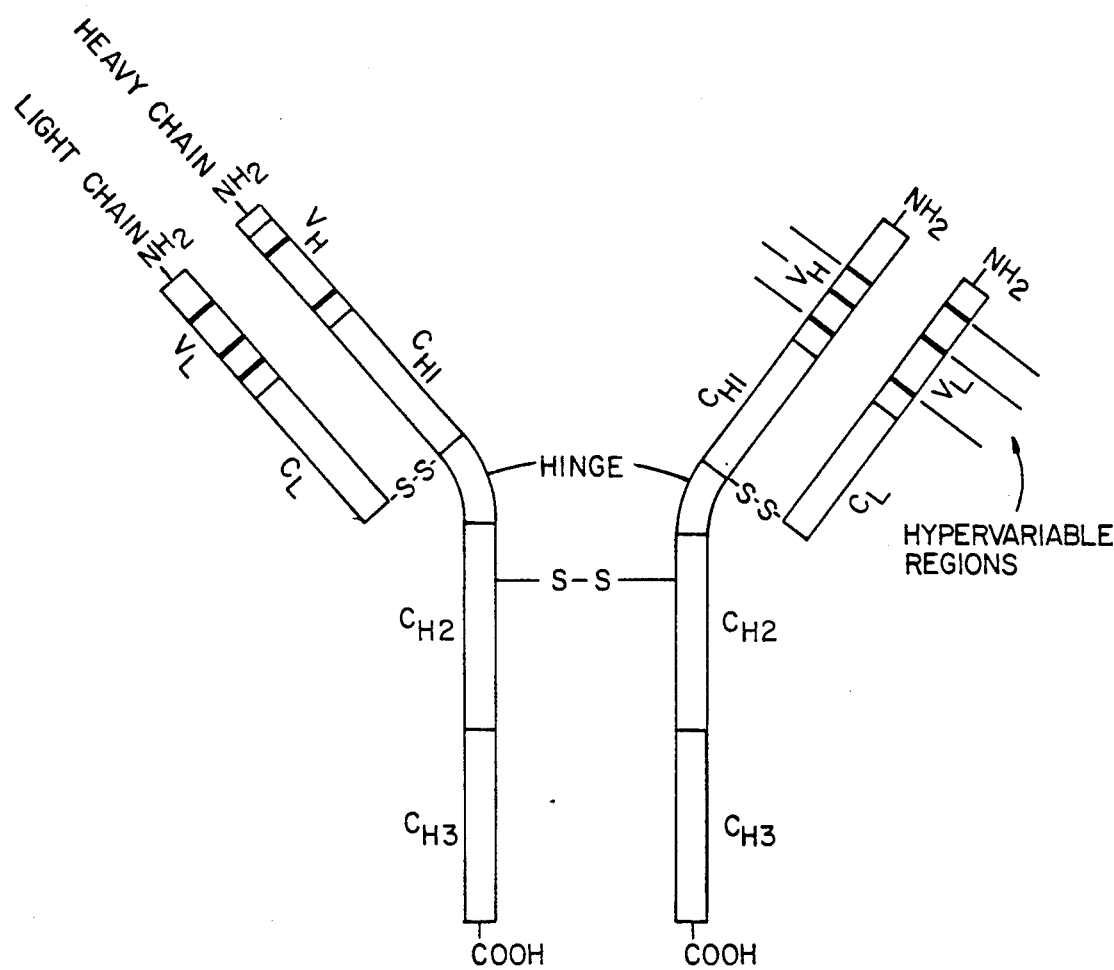
FIG. 1 is a representation of an antibody molecule.

This invention is based on the finding that the variable region of an antibody chain, when joined as part of a contiguous polypeptide to a polypeptide other than the corresponding constant region of that antibody chain, retains its binding function and its specificity. As a result, a protein which has diagnostic or therapeutic application can be produced prefitted with an antibody binding site of desired specificity and delivered to selected sites in the body.

Chimeric antibodies of this invention can be comprised of at least one chain which is a chimeric or recombinant polypeptide including the variable region of a chain of an immunoglobulin and a polypeptide other than the constant region of the immunoglobulin. The chimeric antibodies can also be comprised of the variable region of a chain of immunoglobulin; at least a portion of the constant region of an immunoglobulin chain; and an extrinsic polypeptide. The chimeric polypeptide chain is associated with a (nonchimeric) counterpart chain to form a functional antibody site.

In one embodiment, a monovalent chimeric antibody of the present invention is comprised of the variable region ($V_H$) of a heavy chain of an immunoglobulin; the variable region ($V_L$) of a light chain of the same immunoglobulin; the constant region ($C_L$) of an immunoglobulin light chain and an extrinsic polypeptide (X). A chimeric antibody having these components can be represented by the general formula: $V_H C_L X — V_L C_L$. The heavy chain regions can be from an alpha, a delta, an epsilon, a gamma or a mu chain; the light chain regions can be from a kappa light chain or a lambda light chain. The extrinsic polypeptide X can be linked to the polypeptide $V_H C_L$ through a peptide linker. In one embodiment, the monovalent chimeric antibody represented by the general formula $V_H C_L X — V_L C_L$ is specific for an epitope of a cell surface antigen, which can be, for example, tumor cell associated. The polypeptide X can be for example, a metal chelator, such as metallothionein, or a cytotoxin, such as ricin, diphtheria toxin or the A chain of diphtheria toxin.

In another embodiment of this invention, the monovalent chimeric immunoglobulin can be comprised of a light chain of an immunoglobulin associated with a hybrid heavy chain of an immunoglobulin to form a functional antigen-binding molecule. The hybrid heavy chain in this case is comprised of the variable region of a heavy chain of the immunoglobulin; at least a portion of the constant region of a light chain (either kappa or lambda) of the immunoglobulin; and a pharmacologically active polypeptide, which can be linked to the constant region of the light chain through a peptide linker.

In still another embodiment, the chimeric immunoglobulin of this invention is monovalent and can be represented by the formula: $V_H C_{H1} C_{H2} X — V_L C_L$. In this embodiment, the components of the chimeric immunoglobulin are the variable region ($V_H$) of a heavy chain of an immunoglobulin; the constant region ($C_L$) of the light chain of the same immunoglobulin; a portion of the constant region ($C_{H1} C_{H2}$) of a heavy chain which encompasses the $C_{H1}$ constant domain and at least a portion of the $C_{H2}$ constant domain; and at least the active portion of an extrinsic polypeptide (X).

A monovalent chimeric immunoglobulin of the present invention can also be comprised of the heavy chain ($V_H C_H$) of an immunoglobulin; the light chain ($V_L C_L$) of the same immunoglobulin; and an extrinsic polypeptide (X).

Divalent chimeric immunoglobulins represent another embodiment of the present invention. For example, they can be represented by the formula $(V_H C_{H1} C_{H2} X — V_L C_L)_2$. In this case, the chimeric immunoglobulins are comprised of the variable region ($V_H$) of a heavy chain of an immunoglobulin ; the variable region ($V_L$) of a light chain of the same immunoglobulin; a portion ($C_{H1} C_{H2}$) of the constant region of a heavy chain which encompasses the $C_{H1}$ constant domain and at least a portion of the $C_{H2}$ constant domain; the constant region ($C_L$) of an immunoglobulin light chain; and at least the active portion of an extrinsic polypeptide (X).

As is the case for monovalent chimeric antibodies of this invention, the heavy chain regions of the divalent chimeric antibodies can be from an alpha, a delta, an epsilon, a gamma or a mu chain and the light chain regions can be from a kappa light chain or a lambda light chain. Here, too, the extrinsic polypeptide can be any polypeptide other than polypeptides from which the immunoglobulin binding site is derived. For example, the extrinsic polypeptide can be a metal chelator (e.g., metallothionein), a cytotoxin (e.g., ricin, diphtheria toxin, the A chain of diphtheria toxin) or other polypeptide which has diagnostic or therapeutic application. The extrinsic polypeptide can be linked to the portion ($C_{H1} C_{H2}$) of the constant region of a heavy chain through a peptide linker.

The chimeric antibody is produced by recombinant DNA techniques. Maniatis, T. et al., *Molecular Cloning, A laboratory Manual*, Cold Spring Harbor, (1982). Expression vectors having fused gene DNA sequences encoding the chimeric chains are used to transform appropriate recipient cells for expression of the antibody chain. Recipient cells must be capable of antibody production and can be either mammalian cells (e.g., B lymphocytes; hybridomas such as B lymphocytes fused with immortalizing cells; myeloma cells) or yeast or bacterial cells which are transformed with vectors having the genes encoding the chimeric antibody and are capable of expressing them.

In one embodiment, the chimeric gene encoding a chimeric chain contains genes coding for the variable region of a heavy chain ($V_H$) linked to the constant region of a light chain ($C_L$). A gene encoding the selected extrinsic polypeptide or protein (X) is positioned 3' to the constant region. In this construction the light chain can be of either the kappa or the lambda type. The expressed chain can be represented by the formula $V_H C_L X$. In some constructions DNA sequences encoding a linker polypeptide may be interposed between the constant region and the extrinsic polypeptide. The extrinsic polypeptide can be a cytotoxin such as diphtheria toxin (A chain) to form an immunotoxin. Another example of the extrinsic polypeptide is metallothionein, a heavy metal chelator which is useful for binding nuclides which can be used for tumor imaging and therapy. In addition, it can be an enzyme or a polypeptide capable of changing the physical properties (e.g., cell surface binding properties) of antibodies. Any extrinsic protein or polypeptide can in fact be included in the chimeric antibody and its selection will be determined by its intended application. A specific extrinsic protein may require a peptide linker (e.g., proline) between the light chain constant region ($C_L$) and the protein in order to maintain the activity.

The DNA construct $V_H$—$C_L$-protein will co-express in the cells with a light chain $V_L C_L$ to make the functional (intact) antibody binding site. The host cell can carry the genes for expression of the light chain naturally or can be transformed to express the chain. Alternatively the recombinant chain can be expressed in one cell, the counterpart chain in another, and the two chains can be combined in vitro. Gene sequences for both antibody chains can be engineered into the same vector, which can be transformed into recipient mammalian, yeast or bacterial cells described previously. The $V_H C_L X$—$V_L C_L$ chimera is a monovalent antibody.

In another embodiment, the chimeric DNA sequences encode a chimeric antibody as above except that the first domain of the heavy chain constant region ($C_{H1}$) is substituted for the light chain C region ($C_L$).

Divalent chimeric antibody can be constructed joining an extrinsic protein to a heavy chain $V_H C_{H1} C_{H2}$ portion. The DNA construct contains the $V_H$ region, the $C_{H1}$ constant domain, at least a portion of the $C_{H2}$ constant domain, and the gene encoding the extrinsic protein or polypeptide (X) or at least its active portion. The $C_{H1}$ and $C_{H2}$ domains are needed to provide the disulfide bridge region for association of heavy chains. The DNA construct $V_H$—$C_{H1} C_{H2}$—X will co-express in the cells with a light chain $V_L$—$C_L$ to make the functional (intact) antibody binding site. A peptide linker may be needed between $C_{H1} C_{H2}$ and the polypeptide X to maintain the activity. The chimeric antibody made in this way is divalent in nature.

It is possible to use either of at least two approaches to constructing a chimeric antibody having the structure, for example, $V_H$—$C_L$—X. In the first method, the gene encoding the extrinsic protein is located in the N-terminal portion of $C_L$. In the second method, the gene is located at the end of the intact $C_L$.

Divalent chimeric antibodies can be made of dual specificity. Two binding sites of different specificities can also be joined.

Chimeric antibodies of this invention are constructed using standard genetic engineering methods. See, for example, by recombinant DNA techniques. Maniatis, T. et al., *Molecular Cloning, A Laboratory Manual*, Cold Spring Harbor (1982). For example, a chimeric gene encoding the variable region of a heavy chain ($V_H$) and the constant region of a kappa light chain ($C_{LK}$) is constructed. Plasmids bearing the chimeric gene and a selectable marker, such as Eco gpt, are then constructed and transfected into mouse myeloma cells by protoplast fusion. Schaffner, W., *Proceedings of the National Academy of Sciences, U.S.A.*, 77:2,163–2,167 (1980); Oi, T., et al., *Proceedings of the National Academy of Sciences, U.S.A.*, 80:825–829 (1983). Transformants containing the selectable marker are then identified and isolated (e.g., in medium containing mycophenolic acid, transformants having the Eco gpt gene can be identified and isolated).

Isolated transformants are analyzed for production of the chimeric protein. This can be carried out, for example, by immunoprecipitation using antiserum reactive with a constant region of the chimeric antibody. It can also be done using anti-idiotype antiserum specific for the $V_H$ protein sequence.

The transformants are subcloned and further analyzed for the chimeric protein expressed. Immunoprecipitation analysis of biosynthetically labelled cells is used for this purpose. The chimeric protein is differentiated from other proteins expressed by means of their mobility on SDS-polyacrylamide gels under non-reducing conditions.

The mRNA encoding the chimeric protein can also be identified, isolated and characterized. The mRNA can be detected, for example, by Northern blot analysis.

This invention will now be further described by the following example, which is not intended to be limiting in any way.

EXAMPLE I

Figure 2:
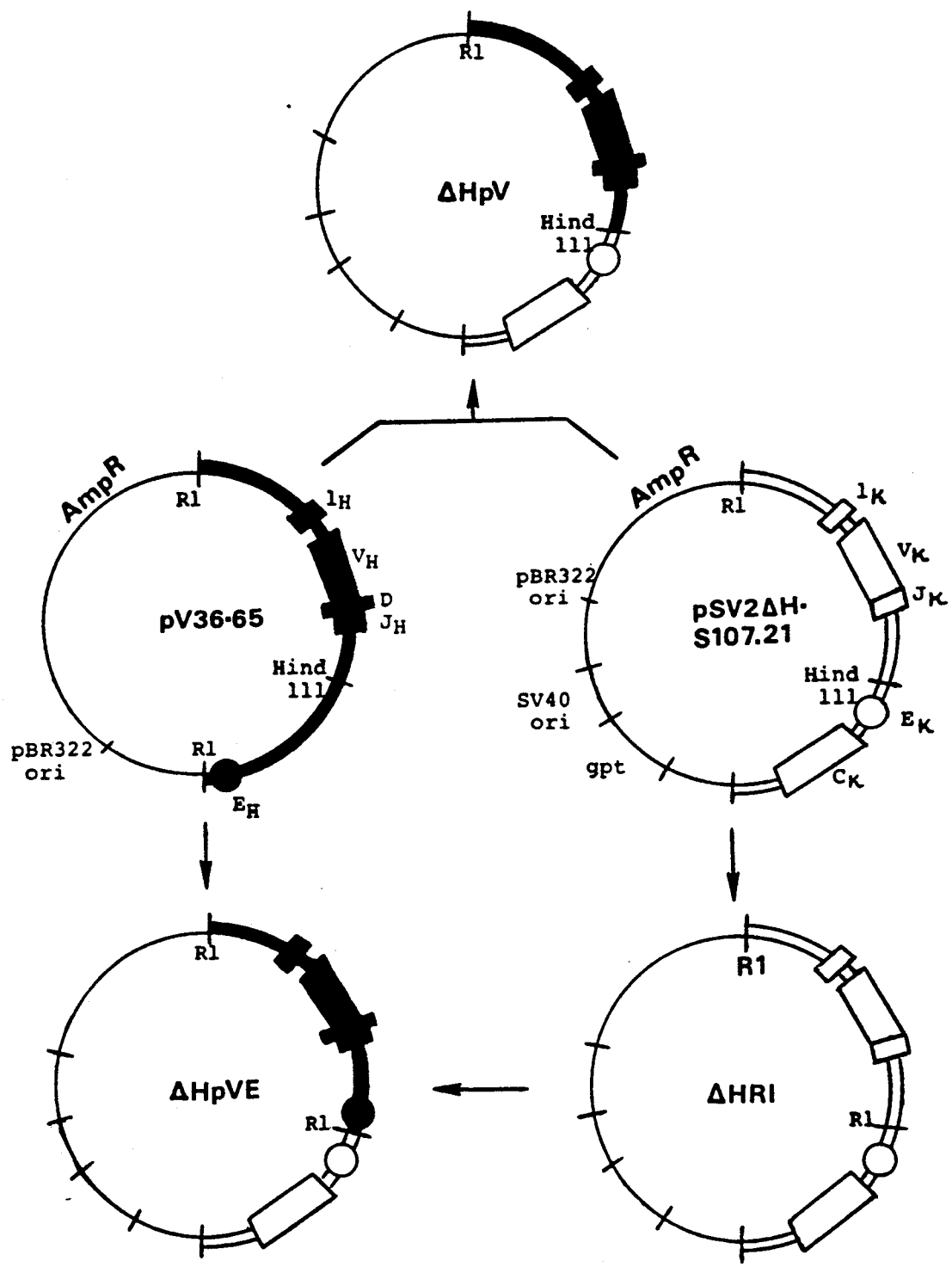
FIG. 2 is a representation of the construction of two plasmids bearing the chimeric DNA sequences encoding a chimeric antibody chain.

I. Construction of $V_H C_L$—$V_L C_L$ Chimeric Antigen Binding Fragment and Demonstration of Antigen-Binding Activity Construction of $V_H C_K$ Containing Plasmids FIG. 2 shows the scheme according to which two plasmids, $\Delta H_p V$ and $\Delta H_p VE$, were constructed bearing the $V_H C_L$ chimeric gene and the selectable marker Eco gpt. Both $\Delta H_p V$ and $\Delta H_p VE$ contain the rearranged 36–65 $V_H$ gene with its 5' flanking sequence, and DNA encoding the C region of the kappa L chain of the S107 Balb/c mouse myeloma cell line. A chimeric intron separates the $V_H$ and $C_L$ genes. This intron includes the putative L chain transcriptional enhancer sequence ($E_K$) in $\Delta H_p V$, and both $E_K$ and $E_H$, the H chain transcriptional enhancer sequence, in $\Delta H_p VE$. $\Delta H_p VE$ has been deposited with the American Type Culture Collection (Rockville, Md.) under deposit number 53128.

pV36-65 contains the 363 bp rearranged $V_H$ gene derived from the hybridoma cell line 36–65. This gene is flanked by 2.4 kbp of upstream sequence and 2.1 kbp of downstream sequence terminating in the $J_H$–$C_{mu}$ intron. Siekevitz et al., *European Journal of Immunology*, 12: 1,023–1,032(1982). pSV2ΔHS107.21 was derived from pSV2-S107 by elimination of one Hind III site. (Oi, V.T. et al., *Proceedings of the National Academy of Sciences, U.S.A.*, 801: 825–829 (1983)). pSV2ΔHS107.21 contains the *E. Coli* xanthine-guanine phosphoribosyl transferase gene (gpt), and the entire rearranged genomic K L chain gene of the S107 myeloma cell line, including the leader ($1_K$), $V_K$, and $C_K$ exons as well as flanking 5' and 3' sequences. Kwan, S. P. et al. *Journal of Experimental Medicine*, 153: 1,366–1,370(1981). The gpt gene confers upon mammalian cells resistance to mycophenolic acid when xanthine is present in the medium. Mulligan, R. C. and Berg, P. Science 209: 1,422–1,427(1980). The SV40 origin of DNA replication (ori) and early promoter are located 5' to the gpt sequence. The S107 K gene is oriented in the opposite direction of gpt. HR1 was constructed from pSV2ΔHS107.21 by converting the Hind III site into an Eco R1 site. To generate $\Delta H_p V$, the Eco R1-Hind III fragment containing the rearranged $V_H$ gene from pV36-65 was substituted for the Eco R1-Hind III fragment containing the rearranged $V_K$ gene in pSV2ΔHS107.21. To generate $\Delta H_p VE$, the Eco R1-Eco R1 fragment containing the rearranged $V_H$ gene from $_p$V36-65 was substituted for the Eco R1-Eco R1 fragment containing the rearranged $V_K$ gene in HR1. In FIG. 2, the H chain exons and introns are represented by filled in boxes and lines; the kappa chain exons and introns are represented by hollow boxes and lines; the H chain enhancer sequence ($E_H$), and the putative K chain enhancer sequence ($E_K$) are represented by a filled in and a hollow circle respectively. Plasmids are not drawn to scale.

$\Delta H_p V$ and $\Delta H_p VE$ were separately transfected into J558L Balb/c mouse myeloma cells by protoplast fusion as described by Oi, V.T. et al., supra. (J558L is a variant of the J558 cell line, and synthesizes and secretes only a lambda chain but no H chain. Lundblad, A. et al., *Immunochemistry* 9: 535–544(1972). Transformants containing the Eco gpt gene were selected in medium containing mycophenolic acid. Ten transformants from each of the two transfection experiments were analyzed for production of $V_H C_K$ by immunoprecipitation with rabbit antiserum specific for the C region of mouse K chain, and separately with rabbit anti-idiotype (Id) antiserum specific for the $V_H$ protein sequence Marshak-Rothstein, A. et al., *Proceedings of the National Academy of Sciences, U.S.A.*, 77: 1,120–1,124 (1980); Kuettner, M. G. et al., *Journal of Experimental Medicine*, 135: 579–595(1972). Six of ten $\Delta H_p VE$ transformants produced a protein reactive with anti-K and anti-Id antisera; only one of ten $\Delta H_p V$ transformants produced such a protein. The relative amounts of the chimaeric protein produced by $\Delta H_p V$ and $\Delta H_p VE$ transformants were not significantly different (not shown). More positive transformants might have occurred when $\Delta H_p VE$ was used than when $\Delta H_p V$ was used because the H chain enhancer is present in $\Delta H_p VE$.

Figure 3:
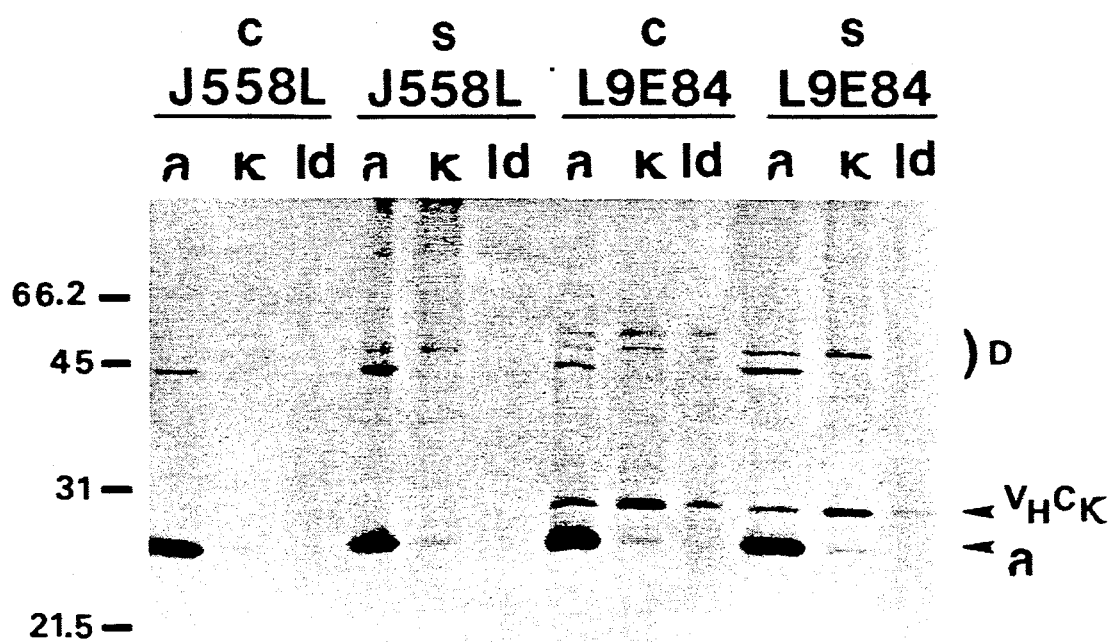
FIG. 3 shows autoradiographs of SDS-polycrylamide gels of biosynthetically labelled J558L and L9E84 cells assayed for production of cytoplasmic and secreted chimeric protein.

Autoradiographs of SDS-Polyacrylamide Gels of Cytoplasmic and Secreted Proteins The $\Delta H_p V$ positive transformant (which was the first to be recovered) was subcloned in soft agarose. Coffino, P. and Scharff, M. D. *Proceedings of the National Academy of Sciences, U.S.A.*, 68: 219–223(1971); Sharon, J. et al., *Proceedings of the National Academy of Sciences, U.S.A.* 76: 1,420–1,424(1979). One clone, L9E84, was further studied. FIG. 3 shows an immunoprecipitation analysis of biosynthetically labelled cells.

Cells were biosynthetically labelled with $^{35}S$ methionine in methionine-free Dulbecco's Modified Eagle's medium (Irvine Scientific, Santa Ana, Calif.) 1 hr for cytoplasmic protein assay and 3 hr for secreted protein assay. Cell extracts were in 0.5% Nonidet P-40. Electrophoresis was in 12.5% SDS-polyacrylamide gels under non-reducing conditions. The positions of MW markers (Biorad), in kd, are shown by lines; the positions of $V_H C_K$ and of lambda L chain are indicated by arrows. (c, cytoplasmic; s, secreted.) Cytoplasmic and secreted proteins from J558L and from L9E84 cells were immunoprecipitated with rabbit anti-mouse Ig antisera and *Staphyloccoccus aureus* (Staph A) and electrophoresed as described by Sharon, J. et al., *Molecular Immunology* 18: 831–846(1981). The antisera used are indicated above each lane. Rabbit anti-mouse K was obtained from Michael Potter under the auspices of NCI contract NO1-CB-25584. Rabbit anti-mouse alpha and lambda (designated $\lambda$) was prepared in the laboratory of S. L. Morrison by Letitia A. Wims. Rabbit anti-Id antiserum was prepared by Larry J. Wysocki. Dimers (D) are indicated.

A protein of the expected Mr (29.5 kd) reactive with anti-K and with anti-Id antisera is present in L9E84 but not in J558L cell extracts. Furthermore, this protein is secreted into the medium (FIG. 3). Immunoprecipitation of $V_H C_K$ from L9E84 culture supernatant by anti-K antiserum removed the species reactive with anti-Id antiserum (not shown). The $V_H C_K$ chimaeric protein can be differentiated from the J558L lambda L chain by its lower mobility in SDS-polyacrylamide gels under non-reducing conditions (FIG. 3.) The upper bands in FIG. 3 are probably covalent dimers (D). From the relative sizes of these putative dimers it seems that $V_H C_K$ can dimerize both with itself and with the J558L lambda L chain.

Figure 3A:
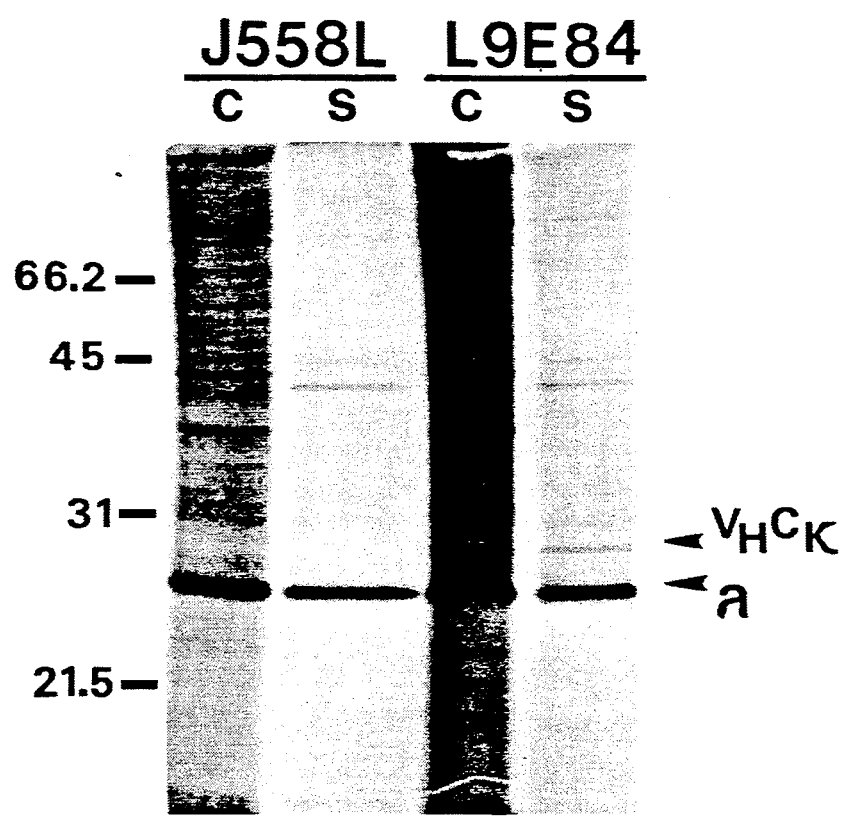
FIG. 3a shows total cytoplasmic and secreted proteins from the two types of cells.

The $V_H C_K$ chimaera comprises about one percent of the biosynthetically labelled L9E84 cell protein and is present in one tenth the amount of J558L lambda L chain. This was determined by densitometer tracing of the autoradiogram (shown in FIG. 3a) of total cytoplasmic and secreted proteins from J558L and from L9E84 cells. Densitometer tracings of L9E84 lanes were done with a Quick Scan from Helena Laboratories. For quantitation peaks from Xerox copies of the scans were cut out and weighed.

Ascites from Balb/c mice injected intraperitoneally with L9E84 cells contain the chimaeric protein, as determined by a radioimmunoassay. This assay measured the ability of the ascites fluid to compete with the $^{125}I$-labelled idiotype-bearing molecule, 36–65 Fab, for the binding of rabbit anti-Id antiserum. Marshak-Rothstein, A. et al., *Proceedings of the National Academy of Sciences U.S.A.* 77: 1,120–1,124 (1980).

Figure 4:
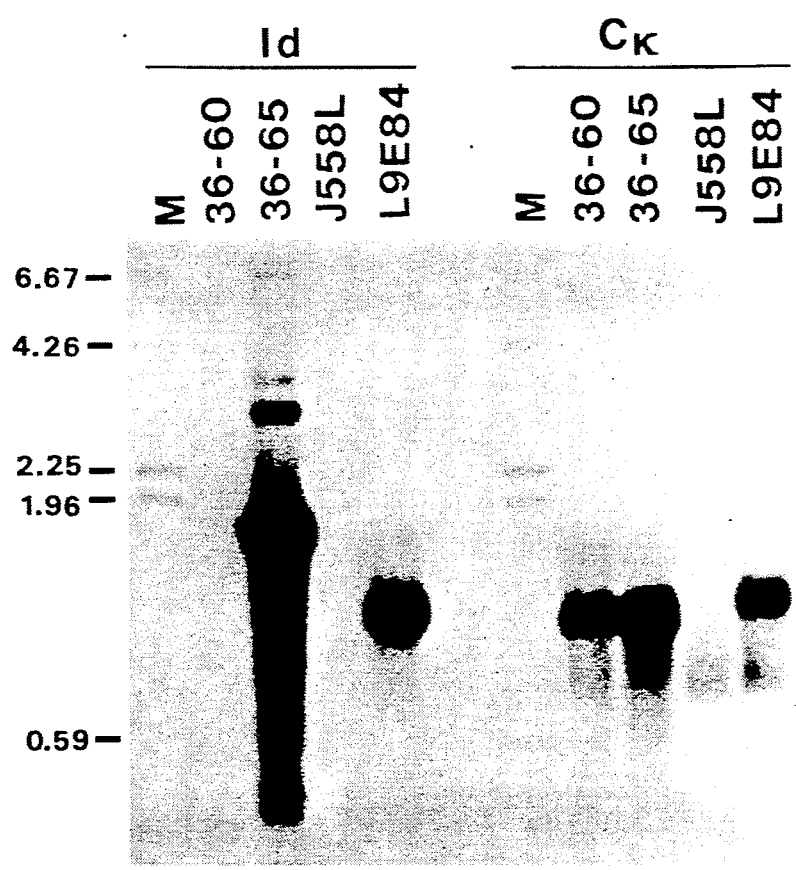
FIG. 4 shows the results of Northern blot analysis of L9E84 and control cell RNA.

Northern Analysis of L9E84 and Control Cell RNA mRNA encoding the $V_H C_K$ protein in L9E84 cells was detected by Northern analysis (FIG. 4). Total cell RNA was prepared from culture cells as described in Maniatis, T. et al., *Molecular Cloning*, p. 196, Cold Spring Harbor Laboratories (1982). The RNA (6 ug/lane) was electrophoresed in duplicate in a 1.2% agarose gel in 10 mM NA Phosphate and transferred to nitrocellulose. Thomas, P. S. *Proceedings of the National Academy of Sciences, U.S.A.*, 77: 5,201–5,205 (1980). The nitrocellulose filter was cut in two and the RNA hybridized to nick translated $^{32}P$ labelled probes. One half was hybridized to a 133 bp $V_H$ probe specific for the $V_H$ gene encoding the anti-Ars idiotype positive H chain. Siekevitz, M. et al., *European Journal of Immunology*, 12: 1,023–1,032 (1982); Siekevitz, M. et al., *European Journal of Immunology* 13: 123–132 (1983). The other was hybridized to a mouse $C_K$ region cDNA probe. The cell lines from which the RNA was derived is indicated above each lane. 36–60 is an A/J derived hybridoma which produces an antibody specific for Ars but devoid of the Ars crossreactive idiotype and uses an unrelated $V_H$ gene. Marshak-Rothstein, A. et al., *Proceedings of the National Academy of Sciences, U.S.A.* 77: 1,120–1,124 (1980). A $^{32}P$-labelled Hind III digest of phage lambda DNA was used as MW markers (M), and fragment sizes are indiced in kbp. The two halves of the nitrocellulose filter were reattached for autoradiography.

An RNA species of the expected size, approximately 1.3 kb, that hybridizes with an Ars idiotype probe (specific for the $V_H$ sequence) and with a K probe (specific for the $C_K$ sequence) is present in L9E84 but not in J558L cells. It is noteworthy that the chimeric intron between $V_H$ and $C_K$ is correctly spliced using the donor splice site from the H chain gene and the acceptor splice site from the K L chain gene. Correct splicing of a chimeric intron was previously observed Chu, G. and Sharp, P. A. *Nature* 289: 378–382 (1981).

Association of $V_H C_K$ With 36–65 KL Chain to Form an Antigen Binding Molecule Whether $V_H C_K$ would associate with the homologous 36–65 derived K L chain to form an antigen binding dimer was also investigated. Such a dimer would be analogous to an Fab fragment, except that it would have two $C_L$ domains. For this experiment the source of 36-65 K chain was cell line 36-65L, a variant of the 36-65 cell line that synthesizes and secretes only the K L chain and no H chain.

Figure 5:
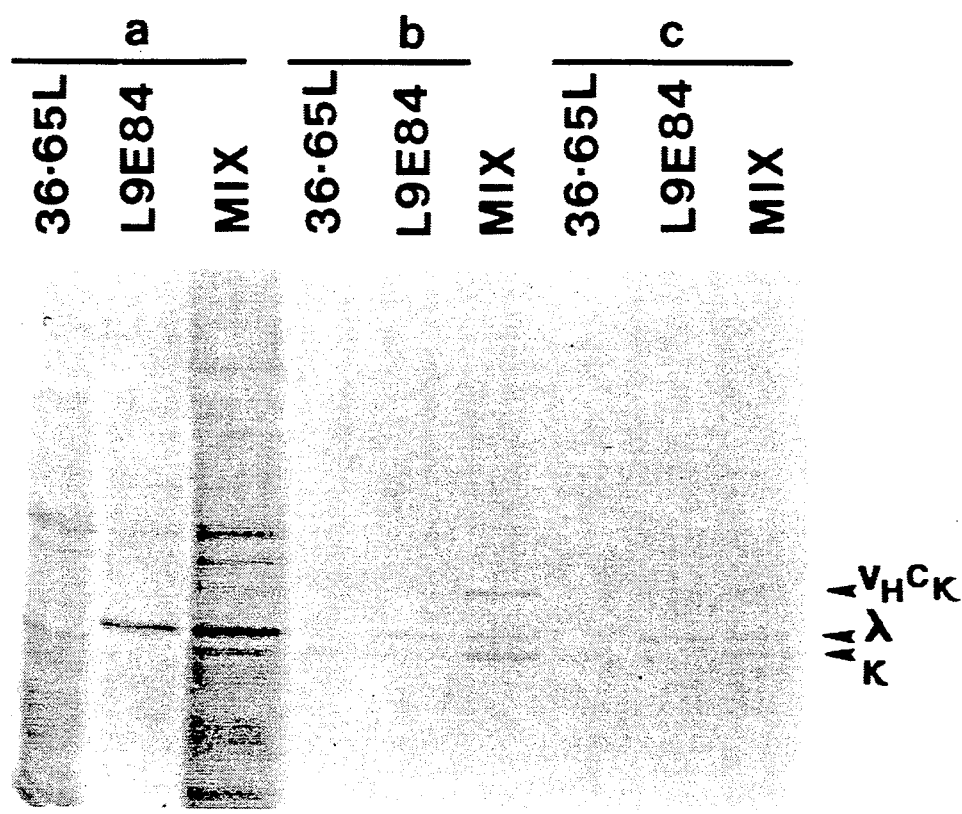
FIG. 5 shows the association of $V_H C_K$ with 36–65 K L chain to form an antigen binding molecule.

L9E84 and 36-65L cells were biosynthetically labelled separately with $^{35}$S methionine and cell extracts were made as described above. Portions of 36-65L, L9E84, and an equal mixture of the two extracts (mix) were made 0.5 M in propionic acid to dissociate interchain noncovalent interactions. After 30 min at room temperature the individual extracts and the mix were dialyzed exhaustively against 5 mM of Na Acetate pH 5.5 at 4° C. to allow association into dimers. Edmundson, A. B. et al., *Biochemistry*, 13: 3,816–3,827 (1974); Peabody, D. S. et al., *Biochemistry* 19: 2,827–2,834 (1980). The dialyzed extracts and the mix were preabsorbed with BGG coupled sepharose for 2.5 hr at 4° C. in Eppendorf tubes. The resin aliquots were washed 5 times with 1 ml of PBS 1 M NaCl 0.5% Nonidet P-40, once with 1 ml of ethylene glycol in the above solution, and once with 1 ml of PBS. Nemethy, G. and Scheraga, H. A., *Journal of Chemistry and Physics*, 36: 3,401–3,417 (1962); Pereira, M. E. A. et al., *Archives of Biochemistry and Biophysics*, 194: 511–525 (1979) Bound protein was eluted with SDS sample buffer at 100° C. Laemmli, J. S., *Nature*, 227: 680–683 (1970). SDS-polyacrylamide gel electrophoresis and autoradiography were as described. Sharon et al., *Molecular Immunology* 18: 831–846 (1981). Densitometer tracing and quantitation were done as described above. (The ratio of methionine residues in $V_HC_K$ to those in 36-65 K is 3:2). FIG. 5, column a, shows dialyzed cell extracts and mix preabsorbed with BGG sepharose. One fifth the amount used for binding to Ars-BGG sepharose was applied to the gel. Column b shows protein bound to Ars-BGG sepharose and column c shows protein bound to Ars-BGG sepharose in the presence of $0.5\times10^{-3}$ M Ars-tyrosine (ABA-tyrosine from Bioresearch, San Rafael, Calif.). The positions of $V_HC_K$, lambda, and 36-65 K chain are indicated.

When $V_HC_K$ and the homologous 36-65 K L chain were associated in vitro, the resulting molecule bound to Ars-bovine gamma globulin (Ars-BGG) sepharose. SDS-polyacrylamide gel electrophoresis of the affinity bound protein (FIG. 5b mix) and the densitometric analysis showed that the $V_HC_K$ and the 36-65 K chain were present in a 1:1 molar ratio. Binding to Ars-BGG sepharose was significantly reduced by competition with Ars-tyrosine hapten (FIG. 5c mix). Lambda chain, in amounts approximately 30 percent of the K or $V_HC_K$ chains, also bound to the Ars-BGG sepharose (FIG. 5b mix). This binding is evidently non-specific, because, unlike that of the K and $V_HC_K$ chains, it is not competed by the Ars-tyrosine hapten (FIG. 5C mix). L9E84 cells produce large amounts of this lambda chain (See FIG. 3b and FIG. 5a), and about 2 percent of the input λ chain binds to the Ars-BGG resin.

These data suggest that a $V_HC_K$ chimaera can associate with L chain in vitro to form an antigen binding molecule. By estimate from densitometer tracing of gel autoradiograms (not shown), 20 to 30 percent of the $V_HC_K$ protein had associated with 36-65 K L chain to form a functional binding site.

Industrial Utility

Chimeric antibodies of this invention have application in the diagnosis and treatment of diseases. Drugs linked with selected antibody binding sites can be made in readily purifiable form and in large quantities. They can be used, for example, for tumor imaging and cancer therapy; for immunodiagnostic assays; and for altering the physical properties of the antibody.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A recombinantly produced monovalent chimeric immunoglobulin of the formula:

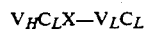

$$V_HC_LX—V_LC_L$$

wherein $V_HC_LX$ represents a chimeric chain and
   a) $V_H$ is the variable region of a heavy chain of an immunoglobulin of selected specificity;
   b) $V_L$ is the variable region of a light chain of the same immunoglobulin of selected specificity;
   c) $C_L$ is the constant region of an immunoglobulin light chain; and
   d) X is a polypeptide moiety selected from the group consisting of a metal chelator, a cytotoxin, and xanthine-guanine phosphoribosyl transferase, or a portion of said polypeptide moiety;
and wherein $V_H$, $C_L$, and X form a contiguous polypeptide and $V_HC_LX$ and $V_LC_L$ form a functional antigen-binding site.

2. A monovalent chimeric immunoglobulin of claim 1 wherein $V_HC_L$ is linked to X through a peptide linker.

3. A monovalent chimeric immunoglobulin of claim 1 wherein $V_H$ and $V_L$ are, respectively, the variable region of a heavy chain and the variable region of a light chain of an immunoglobulin which is specific for an epitope of a cell surface antigen.

4. A monovalent chimeric immunoglobulin of claim 3 wherein the surface antigen is tumor cell associated.

5. A recombinantly produced monovalent chimeric immunoglobulin of claim 1 wherein the metal chelator is metallothionein.

6. A recombinantly produced monovalent chimeric immunoglobulin of claim 1 wherein the cytotoxin is selected from the group consisting of ricin, diphtheria toxin, and the A chain of diphtheria toxin.

7. A monovalent chimeric immunoglobulin of claim 1 wherein $C_L$ is of the kappa type.

8. A recombinantly produced monovalent chimeric immunoglobulin comprising a light chain of an immunoglobulin of selected epitopic specificity and a chimeric immunoglobulin heavy chain which together form a functional antigen-binding molecule, the chimeric heavy chain comprising, from the amino terminus to the carboxyl terminus, the following components, joined so as to form a contiguous polypeptide:
   a) the variable region of a heavy chain of the immunoglobulin of selected specificity;
   b) at least a portion of the constant region of a light chain of an immunoglobulin; and
   c) a polypeptide moiety selected from the group consisting of a metal chelator, a cytotoxin, and xanthine-guanine phosphoribosyl transferase, or a portion of said polypeptide moiety.

9. A combantly produced monovalent chimeric immunoglobulin of claim 8 wherein the polypeptide moiety or portion thereof is linked to component (b) through a peptide linker.

10. A recombinantly produced monovalent chimeric immunoglobulin of claim 8 wherein the immunoglobulin of selected epitopic specificity is specific for an epitope of a cell surface antigen.

11. A recombinantly produced monovalent chimeric immunoglobulin of claim 10 wherein the surface antigen is tumor cell associated.

12. A recombinantly produced monovalent chimeric immunoglobulin of claim 8 wherein the metal chelator is metallothionein.

13. A recombinantly produced monovalent chimeric immunoglobulin of claim 8 wherein the cytotoxin is selected from the group consisting of ricin, diphtheria toxin, and the A chain of diphtheria toxin.

14. A recombinantly produced monovalent chimeric immunoglobulin of claim 8 wherein component (b) is of the kappa type.

15. A recombinantly produced monovalent chimeric immunoglobulin of the formula:

$$V_H C_H - V_L C_L X$$

wherein:
a) $V_H C_H$ is at least a portion of the heavy chain of an immunoglobulin of selected specificity;
b) $V_L C_L$ is a light chain of the same immunoglobulin of selected specificity; and
c) X is a polypeptide moiety selected from the group consisting of a metal chelator, a cytotoxin, and xanthine-guanine phosphoribosyl transferase, or a portion of said polypeptide moiety;
and wherein $V_H C_H$ and $V_L C_L X$ form an antigen-binding site.

16. A recombinantly produced monovalent chimeric immunoglobulin of claim 15 wherein $V_L C_L$ is linked to X through a peptide linker.

17. A recombinantly produced monovalent chimeric immunoglobulin of claim 15 wherein $V_H$ and $V_L$ are, respectively, the variable region of a heavy chain and the variable region of a light chain of an immunoglobulin which is specific for an epitope of a cell surface antigen.

18. A recombinantly produced monovalent chimeric immunoglobulin of claim 17 wherein the surface antigen is tumor cell associated.

19. A recombinantly produced monovalent chimeric immunoglobulin of claim 15 wherein the metal chelator is metallothionein.

20. A recombinantly produced monovalent chimeric immunoglobulin of claim 15 wherein the cytotoxin is selected from the group consisting of ricin, diphtheria toxin, and the A chain of diphtheria toxin.

21. A recombinantly produced divalent chimeric immunoglobulin of the formula:

$$(V_H C_H - V_L C_L X)_2$$

wherein:
a) $V_H C_H$ is the heavy chain of an immunoglobulin of selected specificity;
b) $V_L C_L$ is a light chain of the same immunoglobulin of selected specificity; and
c) X is a polypeptide moiety selected from the group consisting of a metal chelator, a cytotoxin, and xanthine-guanine phosphoribosyl transferase, or a portion of said polypeptide moiety;

and wherein $V_H C_H$ and $V_L C_L X$ form an antigen-binding site.

22. A recombinantly produced monovalent chimeric immunoglobulin of claim 21 wherein $V_L C_L$ is linked to X through a peptide linker.

23. A recombinantly produced monovalent chimeric immunoglobulin of claim 21 wherein the immunoglobulin of selected specificity is specific for an epitope of a cell surface antigen.

24. A recombinantly produced monovalent chimeric immunoglobulin of claim 23 wherein the surface antigen is tumor cell associated.

25. A recombinantly produced monovalent chimeric immunoglobulin of claim 21 wherein the metal chelator is metallothionein.

26. A recombinantly produced monovalent chimeric immunoglobulin of claim 21 wherein the cytotoxin is selected from the group consisting of ricin, diphtheria toxin, and the A chain of diphtheria toxin.

27. A recombinantly produced chimeric antibody having at least one functional antigen-binding site, said site formed by a chimeric polypeptide light chain and a counterpart polypeptide chain, the chimeric chain comprising the variable region of a light chain of an immunoglobulin of selected specificity joined, as part of a contiguous polypeptide, with a polypeptide moiety selected from the group consisting of a metal chelator, a cytotoxin, and xanthine-guanine phosphoribosyl transferase, or a portion of said polypeptide moiety, the variable region present in the counterpart polypeptide being a variable region of the counterpart chain of the immunoglobulin of selected specificity.

28. A recombinantly produced chimeric antibody of claim 27 wherein the variable region of the light chain is linked to the polypeptide moiety or portion thereof through a peptide linker.

29. A recombinantly produced chimeric antibody of claim 27 wherein the immunoglobulin of selected specificity is specific for an epitope of a cell surface antigen.

30. A recombinantly produced chimeric antibody of claim 29 wherein the surface antigen is tumor cell associated.

31. A recombinantly produced chimeric antibody of claim 27 wherein the metal chelator is metallothionein.

32. A recombinantly produced chimeric antibody of claim 27 wherein the cytotoxin is selected from the group consisting of ricin, diphtheria toxin, and the A chain of diphtheria toxin.

33. A recombinantly produced chimeric immunoglobulin antigen-binding fragment of the formula:

$$V_H C_L - V_L C_L$$

wherein:
a) $V_H$ is the variable region of a heavy chain of an immunoglobulin of selected specificity;
b) $V_L$ is the variable region of a light chain of the same immunoglobulin of selected specificity; and
c) $C_L$ is the constant region of an immunoglobulin light chain.

34. A recombinantly produced chimeric immunoglobulin of claim 33 wherein the immunoglobulin of selected specificity is specific for an epitope of a cell surface antigen.

35. A recombinantly produced chimeric immunoglobulin of claim 34 wherein the surface antigen is tumor cell associated.

36. A recombinantly produced chimeric immunoglobulin of claim 33 wherein $C_L$ is of the kappa type.

37. A recombinantly produced chimeric immunoglobulin having at least one chimeric polypeptide chain, said chimeric chain comprising
   a) the variable region encoded by the 363 base pair rearranged $V_H$ gene derived from the hybridoma cell line 36-65;
   b) the constant region of the kappa light chain of the S107 Balb/c mouse myeloma cell line; and
   c) a polypeptide moiety selected from the group consisting of a metal chelator, a cytotoxin, and xanthine-guanine phosphoribosyl transferase, or a portion of said polypeptide moiety.

38. A recombinantly produced chimeric immunoglobulin of claim 37 wherein the metal chelator is metallothionein.

39. A recombinantly produced chimeric immunoglobulin of claim 37 wherein the cytotoxin is selected from the group consisting of ricin, diphtheria toxin, and the A chain of diphtheria toxin.

40. A monovalent chimeric immunoglobulin having at least one chimeric polypeptide chain comprising the variable region encoded by the 363 base pair rearranged $V_H$ gene derived from the hybridoma cell line 36-65 and the constant region of the kappa light chain of the S107 Balb/c mouse myeloma cell line.

41. A recombinantly produced chimeric antibody having at least one functional antigen-binding site, said site formed by a chimeric polypeptide light chain and a counterpart polypeptide chain, the chimeric chain comprising, from the amino terminus to the carboxyl terminus, the following components, joined so as to form a contiguous polypeptide:
   a) the variable region of a light chain of an immunoglobulin of selected specificity; and
   b) at least a portion of the constant region of a heavy chain of an immunoglobulin, the variable region present in the counterpart polypeptide being a variable region of the counterpart chain of the immunoglobulin of selected specificity.

42. A recombinantly produced chimeric antibody of claim 41, the chimeric polypeptide light chain further comprising component (c), wherein (c) is a polypeptide moiety selected from the group consisting of a metal chelator, a cytotoxin, and xanthine-guanine phosphoribosyl transferase, or a portion of said polypeptide moiety.

* * * * *

UNITED STATES PATENT AND TRADEMARK OFFICE
CERTIFICATE OF CORRECTION

PATENT NO. : 5,169,939

DATED : December 8, 1992

INVENTOR(S) : Malcolm L. Gefter, Mark Ptashne, Jacqueline Sharon

It is certified that error appears in the above-identified patent and that said Letters Patent is hereby corrected as shown below:

On title page, item [22]

Filed: Delete "Apr. 9, 1989" and insert ---Jan. 9, 1989---.

Col. 12, claim 9, line 67, delete "combinantly" and insert ---recombinantly---.

Col. 14, claim 22, line 3, delete "monovalent" and insert --divalent--

Col. 14, claim 23, line 6, delete "monovalent" and insert --divalent--

Col. 14, claim 24, line 10, delete "monovalent" and insert ---divalent---.

Col. 14, claim 25, line 13, delete "monovalent" and insert ---divalent---.

Col. 14, claim 26, line 16, delete "monovalent" and insert ---divalent---.

Signed and Sealed this

Seventh Day of December, 1993

Attest:

BRUCE LEHMAN

Attesting Officer

Commissioner of Patents and Trademarks